(12) United States Patent
Tanigawa et al.

(10) Patent No.: US 8,684,931 B2
(45) Date of Patent: Apr. 1, 2014

(54) ULTRASONIC DIAGNOSTIC APPARATUS FOR ELASTICITY IMAGING

(75) Inventors: Shunichiro Tanigawa, Tokyo (JP); Koji Miyama, Tokyo (JP); Seiji Funaya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 550 days.

(21) Appl. No.: 12/868,926

(22) Filed: Aug. 26, 2010

(65) Prior Publication Data

US 2011/0054314 A1    Mar. 3, 2011

(30) Foreign Application Priority Data

Aug. 26, 2009  (JP) ................................ 2009-195004

(51) Int. Cl.
*A61B 8/00*  (2006.01)
(52) U.S. Cl.
USPC ........................... 600/438; 600/443; 382/128
(58) Field of Classification Search
None
See application file for complete search history.

(56) References Cited

U.S. PATENT DOCUMENTS

| | | | |
|---|---|---|---|
| 5,178,147 A | 1/1993 | Ophir et al. | |
| 5,847,281 A * | 12/1998 | Kazys et al. | 73/597 |
| 6,270,459 B1 * | 8/2001 | Konofagou et al. | 600/449 |
| 6,558,324 B1 | 5/2003 | Von Behren et al. | |
| 7,520,855 B2 | 4/2009 | Tamano et al. | |
| 7,628,754 B2 | 12/2009 | Matsumura et al. | |
| 7,678,051 B2 | 3/2010 | Fan et al. | |
| 2007/0032726 A1 | 2/2007 | Osaka et al. | |
| 2008/0051659 A1 * | 2/2008 | Waki et al. | 600/443 |
| 2008/0119732 A1 | 5/2008 | Hiltawsky et al. | |
| 2009/0018444 A1 | 1/2009 | Osaka et al. | |
| 2009/0149752 A1 | 6/2009 | Osaka et al. | |
| 2011/0019894 A1 * | 1/2011 | Tanigawa | 382/131 |
| 2012/0016237 A1 * | 1/2012 | Tanigawa | 600/438 |
| 2012/0215102 A9 * | 8/2012 | Tanigawa | 600/438 |

FOREIGN PATENT DOCUMENTS

| | | |
|---|---|---|
| JP | 2005-118152 | 5/2005 |
| JP | 3991282 B2 | 10/2007 |
| JP | 2008073144 A | 4/2008 |

(Continued)

OTHER PUBLICATIONS

Japanese Office Action, Application No. 2009-195004, dated Jul. 7, 2013, pp. 4.

*Primary Examiner* — James Kish
*Assistant Examiner* — Amanda Lauritzen Moher
(74) *Attorney, Agent, or Firm* — Armstrong Teasdale LLP

(57) ABSTRACT

An ultrasonic diagnostic apparatus includes a physical quantity calculator for setting correlation windows to two echo signals obtained by transmission/reception of ultrasound to and from a biological tissue and different in time on the same sound rays and performing a correlation arithmetic operation between the correlation windows to thereby calculate physical quantities related to elasticity of respective regions in the biological tissue, an elastic image data generator for generating elastic image data of the biological tissue with respect to an elastic image forming region of a transmission/reception surface of the ultrasound, based on the physical quantities, a physical quantity average unit for calculating an average of the physical quantities in the elastic image forming region for every frame, a comparator for comparing a value calculated by the physical quantity average unit and a preset average value of the physical quantities, and a notification unit for notifying a result of comparison by the comparator.

16 Claims, 10 Drawing Sheets

(56) References Cited

FOREIGN PATENT DOCUMENTS

| | | |
|---|---|---|
| JP | 2008-126079 | 6/2008 |
| JP | 2008161546 A | 7/2008 |
| JP | 2008259555 A | 10/2008 |
| WO | 2005122907 A1 | 12/2005 |

* cited by examiner

ULTRASONIC DIAGNOSTIC APPARATUS FOR ELASTICITY IMAGING

CROSS REFERENCE TO RELATED APPLICATIONS

This application claims the benefit of Japanese Patent Application No. 2009-195004 filed Aug. 26, 2009, which is hereby incorporated by reference in its entirety.

BACKGROUND OF THE INVENTION

The present invention relates to an ultrasonic diagnostic apparatus, and particularly to an ultrasonic diagnostic apparatus that displays an elastic image indicative of the hardness or softness of a biological tissue.

An ultrasonic diagnostic apparatus, which combines a normal B-mode image and an elastic image indicative of the hardness or softness of a biological tissue together and displays the result of combination, has been disclosed in, for example, Japanese Unexamined Patent Publication No. 2005-118152 or the like. In this type of ultrasonic diagnostic apparatus, the elastic image is generated in the following manner. First, ultrasound is transmitted and received to and from the biological tissue while repeating pressure from a body surface by an ultrasonic probe and its relaxation to thereby acquire echo signals. Then, a physical quantity related to the elasticity of the biological tissue is calculated based on the acquired echo signals. The physical quantity is converted into hue information to thereby form a color elastic image. Incidentally, for example, a displacement based on deformation of the biological tissue (hereinafter called simply "displacement") or the like is calculated as the physical quantity related to the elasticity of the biological tissue.

One example of a method for calculating the physical quantity will be explained a little more. Correlation windows each having a width corresponding to a predetermined number of data are first respectively set to two echo signals on the same sound rays, different in time from each other. A correlation arithmetic operation is performed between the correlation windows to calculate the physical quantity. In Japanese Unexamined Patent Publication No. 2008-126079, for example, a correlation arithmetic operation is performed between correlation windows to thereby calculate a shift in waveform between both echo signals. This shift in waveform is assumed to be a displacement.

Incidentally, when deformation of the biological tissue is insufficient as in the case of, for example, lack of the degrees of pressure and its relaxation, or the like, the value calculated by the correlation arithmetic operation may not appear as a difference corresponding to the discrepancy in elasticity of the biological tissue. In this case, the elastic image is not brought to one on which the elasticity of the biological tissue has been reflected accurately.

On the other hand, when the degrees of the pressure and its relaxation are in excess, a lateral shift might occur in the biological tissue. Each echo signal acquired in such a case contains noise due to the lateral shift, so that there is a fear that a correlation coefficient at a correlation arithmetic operation becomes low. There is a fear that when the degrees of the pressure and its relaxation are excessive, deformation of the biological tissue is so excessive that the correlation windows set to the two echo signals are not matched with each other, thus reducing the correlation coefficient. When the correlation coefficient at the correlation arithmetic operation becomes low here, the resulting calculated value cannot be obtained as a calculated value on which the elasticity of the biological tissue has been reflected accurately. Thus, as the correlation coefficient at the correlation arithmetic operation becomes lower, the elastic image on which the elasticity of the biological tissue has been reflected accurately cannot be obtained.

The intensity of each echo signal becomes insufficient in a region small in the number of ultrasound reflectors and at a deep portion of a biological tissue, to which transmit ultrasound is hard to achieve due to its attenuation. Thus, a correlation coefficient at a correlation arithmetic operation on each echo signal insufficient in signal intensity becomes low. When the direction of the pressure by the ultrasonic probe and its relaxation does not coincide with an ultrasonic sound ray direction, the above-described lateral shift occurs. Therefore, a correlation coefficient at a correlation arithmetic operation on each echo signal acquired in such a state also becomes low. Accordingly, an elastic image on which the elasticity of the biological tissue has been reflected accurately cannot be obtained even in these cases.

Even though, however, the elastic image on which the elasticity of the biological tissue has been reflected accurately in this way are not obtained, it is difficult for an operator who has viewed the elastic image to determine whether it is of the elastic image on which the elasticity of the biological tissue has been reflected accurately.

There has therefore been disclosed in U.S. Pat. No. 6,558,324, a method wherein in order to allow an operator to easily determine whether an elastic image is of an elastic image on which the elasticity of a biological tissue has been reflected accurately, frame-by-frame averages of values each indicative of elasticity obtained by a correlation arithmetic operation are calculated and results of evaluations of "H" (high), "M" (medium) and "L" (low) are displayed with respect to their average values.

Since, however, U.S. Pat. No. 6,558,324 aims to detect that the elastic image has been formed in a state in which deformation of the biological tissue is insufficient, a worse evaluation ("L" if described concretely) is made as the average value becomes lower. On the other hand, if the average value is high, then the evaluation of "H" is made. Even when, however, the pressure to the biological tissue and its relaxation are performed excessively and the calculated value obtained by the correlation arithmetic operation low in correlation coefficient is included as described above, the elastic image on which the elasticity of the biological tissue has been reflected accurately, is not reached. Therefore, the method of U.S. Pat. No. 6,558,324 may become insufficient to make a decision as to whether the elastic image on which the elasticity of the biological tissue has been reflected accurately is reached and may lack the correctness of its decision.

It is desirable that the problems described previously are solved.

BRIEF DESCRIPTION OF THE INVENTION

The invention according to a first aspect provides an ultrasonic diagnostic apparatus including a physical quantity calculator for setting correlation windows to two echo signals obtained by transmission/reception of ultrasound to and from a biological tissue and different in time on the same sound rays and performing a correlation arithmetic operation between the correlation windows to thereby calculate physical quantities related to elasticity of respective regions in the biological tissue; an elastic image data generator for generating elastic image data of the biological tissue with respect to an elastic image forming region of a transmission/reception surface of the ultrasound based on the physical quantities; a physical quantity average unit for calculating an average of the physical quantities in the elastic image forming region for every frame; a comparator for comparing a value calculated by the physical quantity average unit and a preset average value of the physical quantities; and a notification unit for notifying a result of comparison by the comparator.

According to the invention of a second aspect, there is provided an ultrasonic diagnostic apparatus wherein in the invention according to the first aspect, the physical quantity average unit calculates an average of physical quantities obtained with respect to correlation windows in which a correlation arithmetic operation on correlation coefficients each greater than or equal to a predetermined threshold value is performed.

The invention according to a third aspect provides an ultrasonic diagnostic apparatus wherein in the invention according to the first or second aspect, the comparator calculates, as the result of comparison, a ratio of the value calculated by the physical quantity average unit to the preset average value of the physical quantities.

The invention according to a fourth aspect provides an ultrasonic diagnostic apparatus wherein in the invention according to any one of the first to third aspects, results of comparisons obtained every frame by the comparator are averaged over a plurality of frames and notified to the notification unit.

The invention according to a fifth aspect provides an ultrasonic diagnostic apparatus including a physical quantity calculator for setting correlation windows to two echo signals obtained by transmission/reception of ultrasound to and from a biological tissue and different in time on the same sound rays and performing a correlation arithmetic operation between the correlation windows to thereby calculate physical quantities related to elasticity of respective regions in the biological tissue; an elastic image data generator for generating elastic image data of the biological tissue with respect to an elastic image forming region of a transmission/reception surface of the ultrasound based on the physical quantities; a correlation coefficient average unit for calculating every frame an average in the elastic image forming region, of correlation coefficients at the correlation arithmetic operation between the correlation windows; and a notification unit for notifying a result of calculation by the correlation coefficient average unit.

The invention according to a sixth aspect provides an ultrasonic diagnostic apparatus wherein in the invention according to the fifth aspect, results of calculations obtained every frame by the correlation coefficient average unit are averaged over a plurality of frames and notified to the notification unit.

The invention according to a seventh aspect provides an ultrasonic diagnostic apparatus including a physical quantity calculator for calculating physical quantities related to elasticity of respective regions in a biological tissue, based on two echo signals obtained by transmission/reception of ultrasound to and from the biological tissue and different in time on the same sound rays; an elastic image data generator for generating elastic image data of the biological tissue with respect to an elastic image forming region of a transmission/reception surface of the ultrasound based on the physical quantities; a physical quantity average unit for calculating every frame an average in the elastic image forming region, of physical quantities obtained with respect to correlation windows in which a correlation arithmetic operation on correlation coefficients greater than or equal to a predetermined threshold value is performed; a ratio calculator for calculating a ratio of a value calculated by the physical quantity average unit to a preset average value of the physical quantities; a correlation coefficient average unit for calculating every frame an average in the elastic image forming region, of the correlation coefficients at the correlation arithmetic operation between the correlation windows; a multiplier for multiplying the calculated value of the ratio calculator and the calculated value of the correlation coefficient average unit by each other; and a notification unit for notifying a result of multiplication by the multiplier.

The invention according to an eighth aspect provides an ultrasonic diagnostic apparatus wherein in the invention according to the seventh aspect, results of calculations obtained every frame by the multiplier are averaged over a plurality of frames and notified to the notification unit.

The invention according to a ninth aspect provides an ultrasonic diagnostic apparatus wherein in the invention according to the seventh or eighth aspect, the multiplier performs a weighted arithmetic operation on the calculated value of the ratio calculator and the calculated value of the correlation coefficient average unit.

The invention according to a tenth aspect provides an ultrasonic diagnostic apparatus including a physical quantity calculator for calculating physical quantities related to elasticity of respective regions in a biological tissue, based on two echo signals obtained by transmission/reception of ultrasound to and from the biological tissue and different in time on the same sound rays; an elastic image data generator for generating elastic image data of the biological tissue in an elastic image forming region of a transmission/reception surface of the ultrasound, based on the physical quantities; a physical quantity average unit for calculating every frame an average in the elastic image forming region, of physical quantities obtained with respect to correlation windows in which a correlation arithmetic operation on correlation coefficients greater than or equal to a predetermined threshold value is performed; a ratio calculator for calculating a ratio of a value calculated by the physical quantity average unit to a preset average value of the physical quantities; a correlation coefficient average unit for calculating every frame an average in the elastic image forming region, of the correlation coefficients at the correlation arithmetic operation between the correlation windows; a multiplier for multiplying the calculated value of the ratio calculator and the calculated value of the correlation coefficient average unit by each other; a notification unit capable of notifying a result of calculation by the ratio calculator, a result of calculation by the correlation coefficient average unit or a result of multiplication by the multiplier by switching; and an operation unit for inputting instructions for switching to the notification unit.

In one embodiment, since the result of comparison between the average value in the elastic image forming region, of the physical quantities of the respective regions in the biological tissue, and the preset average value of the physical quantities is displayed, an operator is able to easily determine whether the degrees of the pressure to the biological tissue and its relaxation are insufficient or excessive. It is thus possible to evaluate from a broad standpoint than conventional one whether the elastic image displayed based on the elastic image data is of the elastic image on which the elasticity of the biological tissue has been reflected accurately.

The average value obtained by calculating the average of the physical quantities obtained with respect to the correlation windows in which the correlation arithmetic operation on the correlation coefficients each greater than or equal to the predetermined threshold value is performed is of an average value obtained by eliminating a displacement of a portion low in correlation coefficient like a portion insufficient in the intensity of each echo signal, a portion which has produced a lateral shift in the biological tissue, or the like. Accordingly, the result of comparison between such an average value and the preset average value (ideal value) of the physical quantities is indicative of whether the pressure to the biological tissue and its relaxation are being respectively performed with suitable intensity. As described above, the operator is able to grasp more accurately from the display of the result of comparison whether the pressure to the biological tissue and its relaxation are being respectively performed with the suitable intensity.

Results of comparisons obtained every frame by the comparator are averaged over a plurality of frames and displayed on the display unit, thereby making it possible to display a stable result of comparison.

In another embodiment, since the result of calculation of the average in the elastic image forming region, of the correlation coefficients at the correlation arithmetic operation between the correlation windows is displayed, an operator is able to evaluate from a standpoint different from conventional one whether the elastic image displayed based on the elastic image data is of an elastic image on which the elasticity of a biological tissue has been reflected accurately.

Results of calculations obtained every frame by the correlation coefficient average unit are averaged over a plurality of frames and displayed on the display unit, thereby making it possible to display a stable result of calculation.

In yet another embodiment, the value calculated by the ratio calculator using the average value of physical quantities obtained with respect to correlation windows in which a correlation arithmetic operation on correlation coefficients each greater than or equal to a predetermined threshold value has been performed, and the value calculated by the correlation coefficient average unit are multiplied by each other by the multiplier. A result of this multiplication is displayed. This result of multiplication is equivalent to one to which elements for the degrees of pressure to a biological tissue and its relaxation and elements for correlation coefficients are added. It is thus possible to evaluate from a broader standpoint than conventional one whether an elastic image on which the elasticity of the biological tissue has been reflected accurately is reached.

Results of multiplications obtained every frame by the multiplier are averaged over a plurality of frames and displayed on the display unit, thereby making it possible to display a stable result of multiplication.

In another embodiment, since the result of calculation by the ratio calculator, the result of calculation by the correlation coefficient average unit and the result of multiplication by the multiplier can be displayed by switching, whether an elastic image on which the elasticity of a biological tissue has been reflected accurately is provided can be evaluated from a broad standpoint than conventional one.

Further objects and advantages of the present invention will be apparent from the following description of the preferred embodiments of the invention as illustrated in the accompanying drawings.

DETAILED DESCRIPTION OF THE INVENTION

Embodiments of the invention will hereinafter be explained in detail based on the accompanying drawings.

First Embodiment

Figure 1:
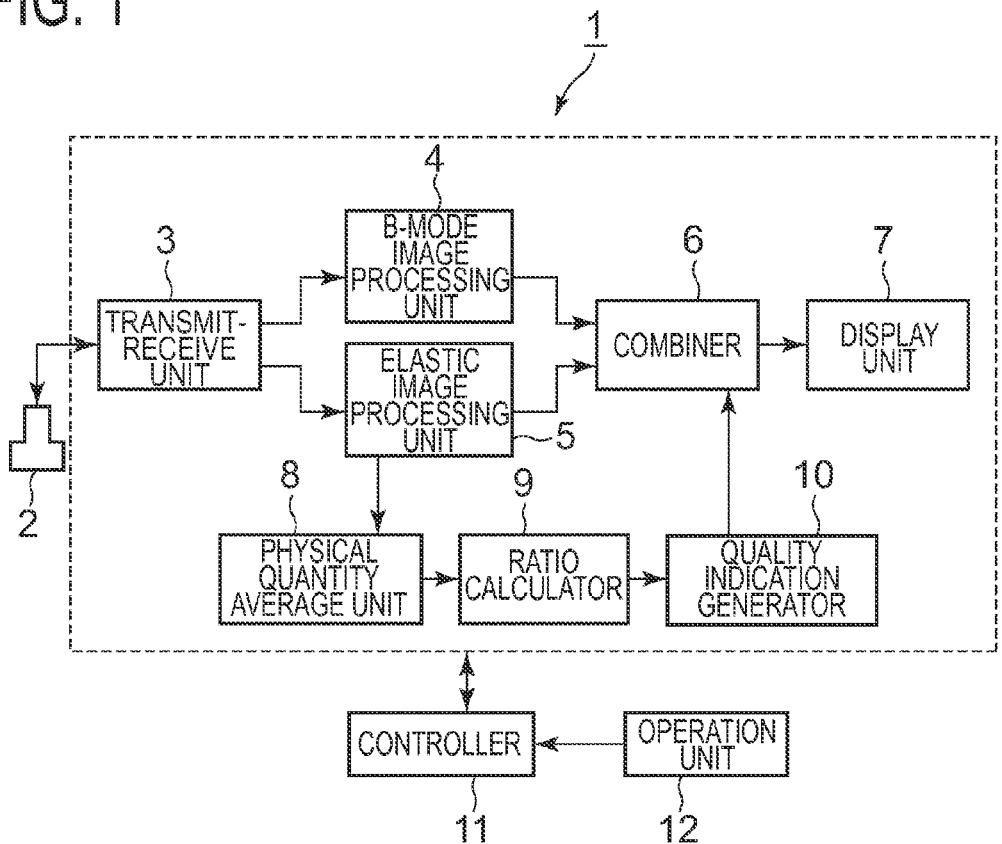
FIG. 1 is a block diagram showing a schematic configuration of a first embodiment of an ultrasonic diagnostic apparatus according to the invention.

A first embodiment will first be explained based on FIGS. 1 through 10. An ultrasonic diagnostic apparatus 1 shown in FIG. 1 is equipped with an ultrasonic probe 2, a transmit-receive unit 3, a B-mode image processing unit 4, an elastic image processing unit 5, a combiner 6, a display unit 7, a physical quantity average unit 8, a ratio calculator 9 and a quality indication generator 10. Further, the ultrasonic diagnostic apparatus 1 includes a controller 11 and an operation unit 12.

The ultrasonic probe 2 transmits ultrasound to a biological tissue and receives its echoes. An elastic image is generated as described later based on echo signals acquired by performing the transmission/reception of the ultrasound while repeating pressure and relaxation in a state in which the ultrasonic probe 2 is being brought into contact with the surface of the biological tissue.

The transmit-receive unit 3 drives the ultrasonic probe 2 under a predetermined scan condition to perform the scanning of the ultrasound every sound ray. The transmit-receive unit 3 performs signal processing such as beamforming processing on each echo signal received by the ultrasonic probe 2. The echo signals subjected to the signal processing by the transmit-receive unit 3 are outputted to the B-mode image processing unit 4 and the elastic image processing unit 5. The echo signals outputted from the transmit-receive unit 3 may be stored in an unillustrated storage unit as raw data.

Incidentally, the transmit-receive unit 3 separately performs a scan for generating a B-mode image and a scan for generating an elastic image. As the scan for generating the elastic image, scanning is done two times on the same sound ray in a region for generating an elastic image for a subject.

The B-mode image processing unit 4 performs B-mode processing such as logarithmic compression processing, envelop detection processing or the like on the echo signals outputted from the transmit-receive unit 3 to thereby generate B-mode image data. The B-mode image processing unit 4 may, however, generate B-mode image data, based on the echo signals stored as the raw data in the storage unit.

The elastic image processing unit 5 generates elastic image data, based on the echo signals outputted from the transmit-receive unit 3. The elastic image processing unit 5 may however generate B-mode image data, based on the echo signals stored in the storage unit as the raw data in a manner similar to the B-mode image processing unit 4.

Figure 2:
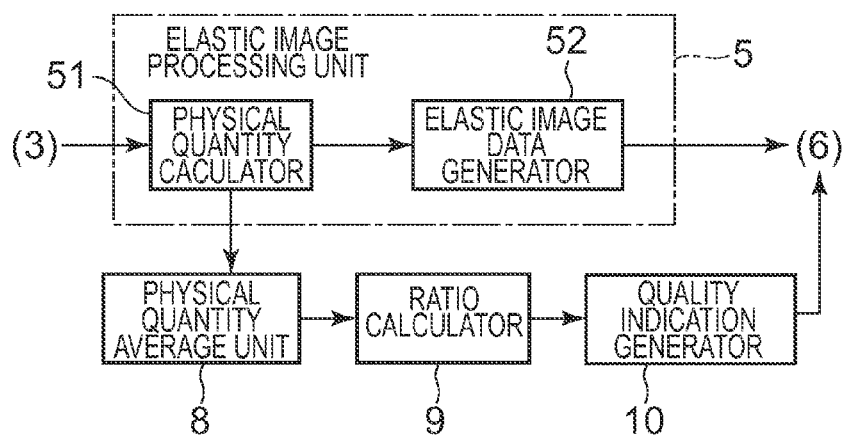
FIG. 2 is a block diagram illustrating a fragmentary configuration of the ultrasonic diagnostic apparatus shown in FIG. 1.
Figure 3:
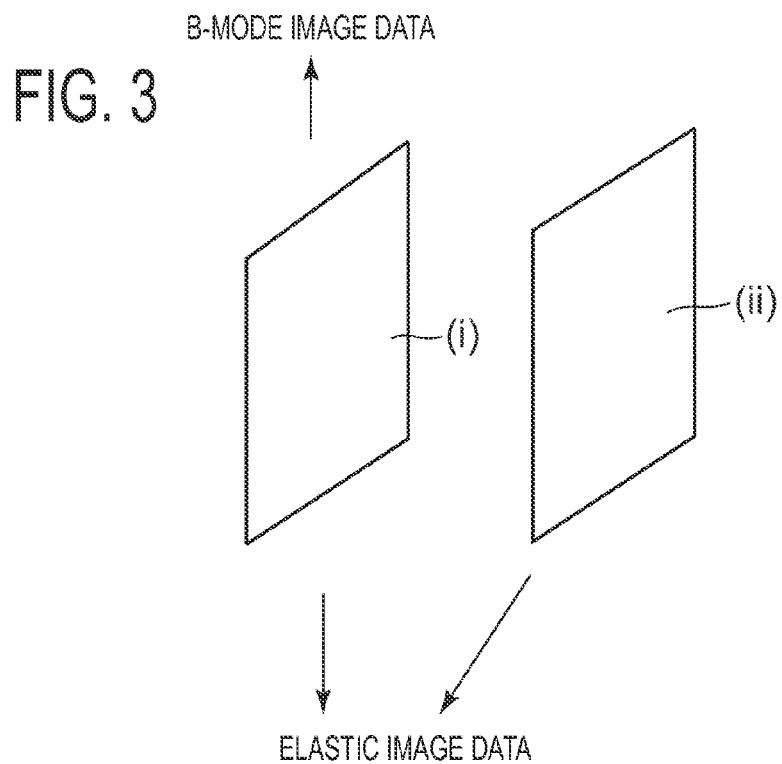
FIG. 3 is a diagram for describing the generation of B-mode image data and elastic image data.

The elastic image processing unit 5 will be explained in a little more detail. As shown in FIG. 2, the elastic image processing unit 5 has a physical quantity calculator 51 and an elastic image data generator 52. The physical quantity calculator 51 calculates displacements (hereinafter called simply "displacements") due to deformation of respective parts or regions of a biological tissue, produced by the pressure by the ultrasonic probe 2 and its relaxation, as physical quantities related to the elasticity of the respective regions in the biological tissue. The physical quantity calculator 51 calculates displacements, based on two echo signals on the same sound rays that belong to two frames (i) and (ii) different in time as shown in FIG. 3. As will be described later, correlation windows W1 and W2 are set to the echo signals (refer to FIG. 5). A correlation arithmetic operation is performed between these correlation windows W1 and W2 to calculate each displacement. Then, the elastic image data generator 52 generates elastic image data corresponding to one pixel, based on the displacement. The physical quantity calculator 51 is one example illustrative of an embodiment of a physical quantity calculator in the invention.

The elastic image data generator 52 converts the displacement calculated by the physical quantity calculator 51 into hue information and generates elastic image data about an elastic image generation region (region of interest R to be described later in the present embodiment) at a transmission/reception surface of ultrasound. The elastic image data generator 52 is one example illustrative of an embodiment of an elastic image data generator in the invention.

Incidentally, as shown in FIG. 3, elastic image data corresponding to one frame is generated from the echo signals that belong to the two different frames (i) and (ii). On the other hand, B-mode image data is generated from the echo signal of either one of the frames (i) and (ii).

Figure 4:
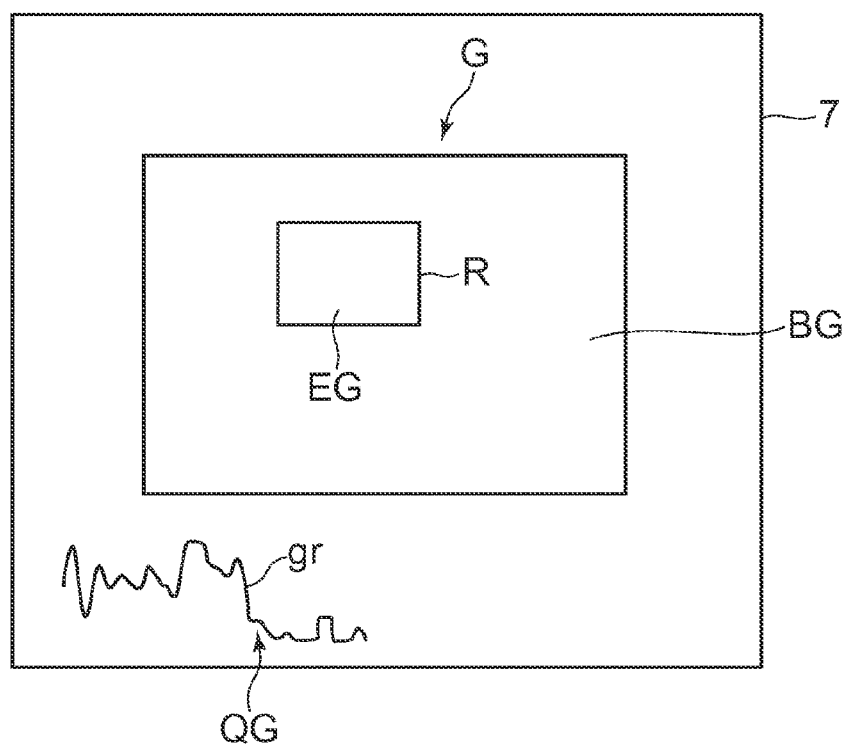
FIG. 4 is a diagram showing one example of a display of a display unit in the ultrasonic diagnostic apparatus shown in FIG. 1.

Now, in the present embodiment, a region of interest (ROI) R is set onto a B mode image BG displayed on the display unit 7 as shown in FIG. 4. The elastic image data is formed in the region of interest R. The region of interest R is one example illustrative of an embodiment of an elastic image forming region in the invention. The invention is however not limited to where the elastic image is generated with respect to part of the B-mode image BG in this way, but the elastic image data may be formed over the entire B-mode image BG.

The B-mode image data generated by the B-mode image processing unit 4 and the elastic image data generated by the elastic image processing unit 5 are combined together by the combiner 6. Described concretely, the combiner 6 adds the B-mode image data and the elastic image data corresponding to one frame together to generate ultrasonic image data corresponding to one frame displayed on the display unit 7. Then, the ultrasonic image data obtained at the combiner 6 is displayed on the display unit 7 as an ultrasonic image G obtained by combining a monochrome B-mode image BG and a color elastic image EG as shown in FIG. 4. In the present embodiment, the elastic image EG is displayed within the region of interest R in a translucent form (in a state in which the background B-mode image is transparent).

Further, a quality graphics or indication QG to be described later is displayed on the display unit 7. The display unit 7 is one example illustrative of an embodiment of a notification unit in the invention.

The physical quantity average unit 8 calculates the average of displacements calculated for every pixel in the region of interest R for every frame. A value calculated by the physical quantity average unit 8 is assumed to be an average value $Xr_{AV}$. The physical quantity average unit 8 is one example illustrative of an embodiment of a physical quantity average unit in the invention.

The ratio calculator 9 calculates a ratio Ra of the average value $Xr_{AV}$ to an ideal value $Xi_{AV}$ of the average of displacements and further performs an arithmetic operation of (equation 1) as will be described later. The ratio calculator 9 is one example illustrative of embodiments of a comparator and a ratio calculator in the invention. The ideal value $Xi_{AV}$ is one example illustrative of an embodiment of the preset average value of physical quantities in the invention.

Here, the ideal value $Xi_{AV}$ corresponds to the average value of displacements obtained in an arbitrarily set region where the pressure to the biological tissue by the ultrasonic probe 2 and its relaxation are performed upon transmission/reception of ultrasound with such an intensity that an elastic image on which the elasticity of the biological tissue has been reflected more accurately can be obtained. The ideal value $Xi_{AV}$ is of a value obtained from experience by performing experiments on a phantom or the like comprised of, for example, a portion of the same hardness as a tumor, a portion of the same hardness as a normal tissue, etc. The ideal value $Xi_{AV}$ may be set at the operation unit 12 by an operator or may be stored in the apparatus as a default.

As shown in FIG. 4, the quality indication generator 10 generates the quality indication QG displayed on the display unit 7 along with the ultrasonic image G. In the present embodiment, the quality indication QG includes a graph gr in which its horizontal axis indicates time and its vertical axis indicates a quality value Qn calculated for every frame as will be described later. The generation of the quality indication QG will be described in detail later.

The controller 11 includes a CPU (Central Processing Unit). The controller 11 reads control programs stored in an unillustrated storage unit and causes the same to execute the functions of the respective parts in the ultrasonic diagnostic apparatus 1. The operation unit 9 includes a keyboard and a pointing device (not shown) for causing the operator to input instructions and information.

The operation of the ultrasonic diagnostic apparatus 1 according to the present embodiment will now be explained.

First, the transmit-receive unit 3 transmits ultrasound from the ultrasonic probe 2 to a biological tissue of a subject and acquires its echo signals. At this time, the transmission/reception of the ultrasound is performed through the ultrasonic probe 2 while repeating the pressure to the subject by the ultrasonic probe 2 and its relaxation.

The B-mode image processing unit 4 generates B-mode image data, based on the echo signals. The elastic image processing unit 5 generates elastic image data, based on the echo signals. The B-mode image data and the elastic image data are combined together at the combiner 6, and an ultrasonic image G obtained by combining a B-mode image BG and an elastic image EG together is displayed on the display unit 7 as shown in FIG. 3.

The quality indication QG produced by the quality indication generator 10 is displayed down below the ultrasonic image G at the display unit 7.

Figure 5:
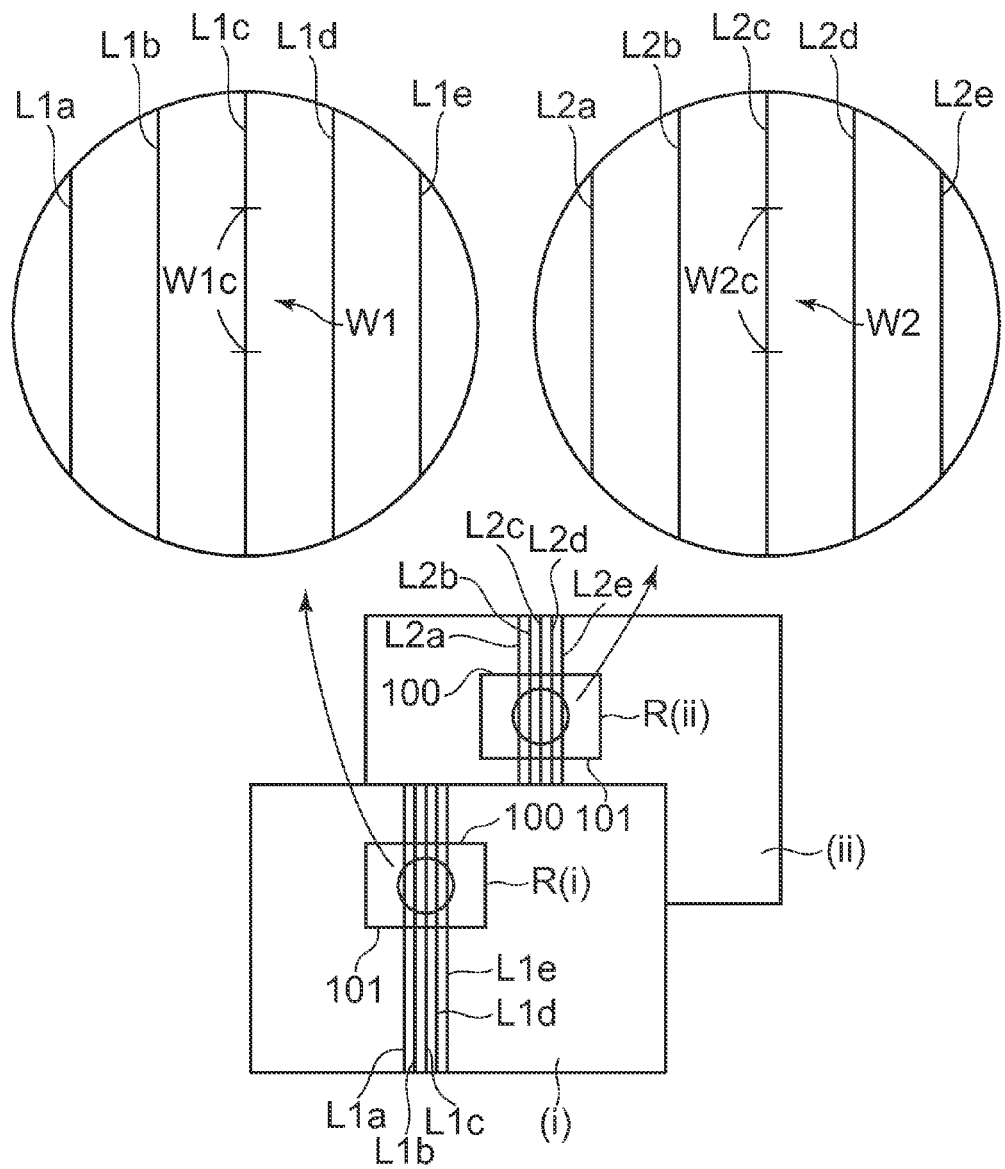
FIG. 5 is a diagram for explaining the calculation of physical quantities at the generation of elastic image data.

The generation of the elastic image data at the elastic image processing unit 5 and the generation of the quality indication QG will be explained in detail. Upon the generation of the elastic image data, the physical quantity calculator 51 sets correlation windows to echo signals of frames (i) and (ii) respectively. Described concretely, the physical quantity calculator 51 sets a correlation window W1 to an echo signal that belongs to a frame (i) and sets a window W2 to each echo signal that belongs to a frame (ii) as shown in FIG. 5. Then, the physical quantity calculator 51 performs a correlation arithmetic operation between the correlation windows W1 and W2 to calculate each displacement.

If explained in concrete terms, the frames (i) and (ii) respectively include echo signals acquired on a plurality of sound rays in FIG. 5. In FIG. 5, five sound rays L1a, L1b, L1c, L1d and L1e are shown as some of the sound rays in the frame (i). Sound rays L2a, L2b, L2c, L2d and L2e are shown as sound rays corresponding to the sound rays L1a through L1e in the frame (ii). Namely, the sound rays L1a and L2a, the sound rays L1b and L2b, the sound rays L1c and L2c, the sound rays L1d and 12d, and the sound rays L1e and L2e respectively correspond to the same sound rays that belong to the two frames different from each other. In FIG. 5, R (i) and R (ii) indicate regions each corresponding to the region of interest R.

Let's assume that for example, a correlation window W1c is set to the echo signal lying on the sound ray L1c as the correlation window W1, and a correlation window W2c is set to the echo signal lying on the sound ray L2c as the correlation window W2. The physical quantity calculator 51 performs a correlation arithmetic operation between the correlation windows W1c and W2c to calculate a displacement. The physical quantity calculator 51 sequentially sets correlation windows W1c and W2c from upper ends 100 of the regions R (i) and R (ii) to their lower ends 101 on the sound rays L1c and L2c to calculate displacements. The physical quantity calculator 51 similarly calculates displacements even with respect to other sound rays in the regions R (i) and R (ii). When the displacements are calculated by the physical quantity in this way, the elastic image data generator 52 generates elastic image data, based on the displacements.

The generation of the quality indication GR will next be explained. Upon the formation of the quality indication GR, the physical quantity average unit 8 first calculates an average value $Xr_{AV}$ of displacements in the regions of interest R (the regions R (i) and R (ii)). Incidentally, since the displacements might become negative, the average value $Xr_{AV}$ is assumed to become negative. Next, the ratio calculator 9 performs an arithmetic operation of $Xr_{AV}/Xi_{AV}$ to calculate the ratio Ra.

Further, the ratio calculator 9 substitutes the ratio Ra into the following equation (1) to obtain a numerical value Y.

$$Y = 1.0 - |\log_{10}|Ra|| \tag{1}$$

where Y is one example illustrative of embodiments of a result of comparison by the comparator and a calculated value of the comparator in the invention.

Figure 6:
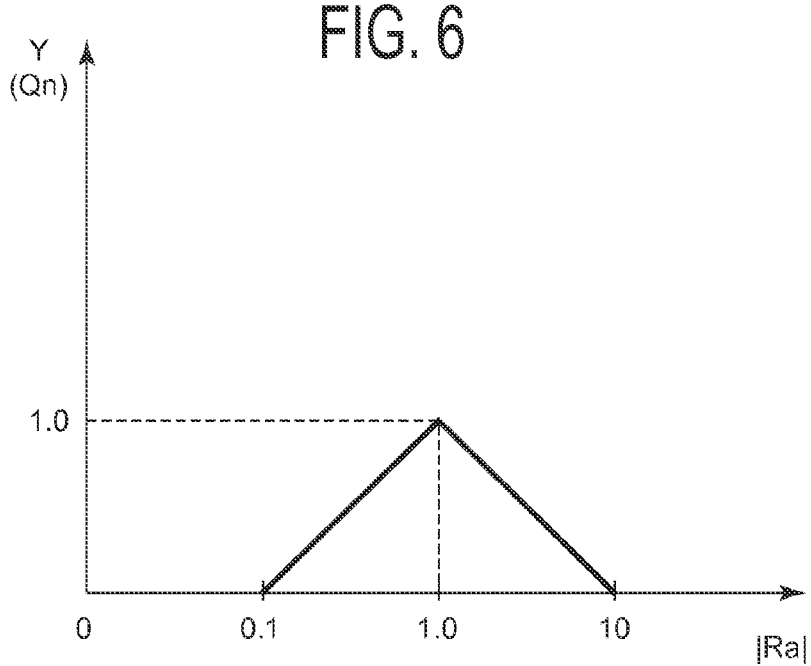
FIG. 6 is a diagram showing a graph of a function used in a ratio calculator.

Incidentally, the equation (1) is one for bringing the ratio Ra to a range of 0 to 1. Y obtained by the equation (1) is equal to the ratio of the average value $Xr_{AV}$ to the ideal value $Xi_{AV}$. If a function expressed in this equation (1) is represented in a graph, it becomes a graph shown in FIG. 6. This Y assumes $0 \le Y \le 1$ as shown in FIG. 6.

Y is assumed to be zero where |Ra| is assumed to be $0.1 \le |Ra| \le 10$ and |Ra| exceeds this range.

The calculated value Y of the ratio calculator 9 is inputted to the quality indication generator 10. Here, the calculated values Y are calculated for every frame. The quality indication generator 10 plots the calculated values Y obtained for every frame as quality values Qn to form a quality indication QG comprised of a graph gr whose horizontal axis indicates time and whose vertical axis is indicative of the quality values Qn. At this time, the quality indication generator 10 calculates the averages of the quality values Qn corresponding to plural frames. Their average values may be plotted. It is thus possible to obtain a stable graph gr free of fluctuations in numeric value.

Since $0 \le Y \le 1$, $0 \le Qn \le 1$ is obtained. This means that as the quality value Qn approaches 1, the quality of an elastic image is satisfactory. On the other hand, this also means that as the quality value Qn approaches zero, the quality of the elastic image becomes worse. Here, it means that the elastic image satisfactory in quality is of an elastic image on which the elasticity of a biological tissue is reflected more accurately. On the other hand, it means that the elastic image worse in quality is not an elastic image on which the elasticity of the biological tissue is accurately reflected.

The relationship between the quality value Qn and the quality of the elastic image will be explained in more detail. As is understood from the graph shown in FIG. 6, Y or Qn becomes 1 where the average value $Xr_{AV}$ is equal to the ideal value $Xi_{AV}$ (i.e., |Ra| is 1). Thus, if Qn is 1 or a value near 1, then the degrees of the pressure to the biological tissue by the ultrasonic probe 2 and its relaxation are suitable, thus resulting in the acquisition of an elastic image EG on which the elasticity of the biological tissue is accurately reflected.

On the other hand, as the average value $Xr_{AV}$ becomes a value away from the ideal value $Xi_{AV}$ (i.e., |Ra| becomes a value away from 1), Qn approaches zero. Here, the average value $Xr_{AV}$ being the value away from the ideal value $Xi_{AV}$ means that the degrees of the pressure to the biological tissue by the ultrasonic probe 2 and its relaxation are insufficient or excessive. Thus, as a result of the fact that as Qn approaches zero, the degrees of the pressure to the biological tissue and its relaxation are lacking or excessive, there is not yet obtained an elastic image EG on which the elasticity of the biological tissue is accurately reflected.

Incidentally, the display of the elastic image EG may not be performed with respect to each frame low in the quality value Qn.

The quality indication QG generated by the quality indication generator 10 is combined with the ultrasonic image G at the combiner 6. Consequently, the quality indication QG is displayed down below the ultrasonic image G at the display unit 7.

Figure 7:
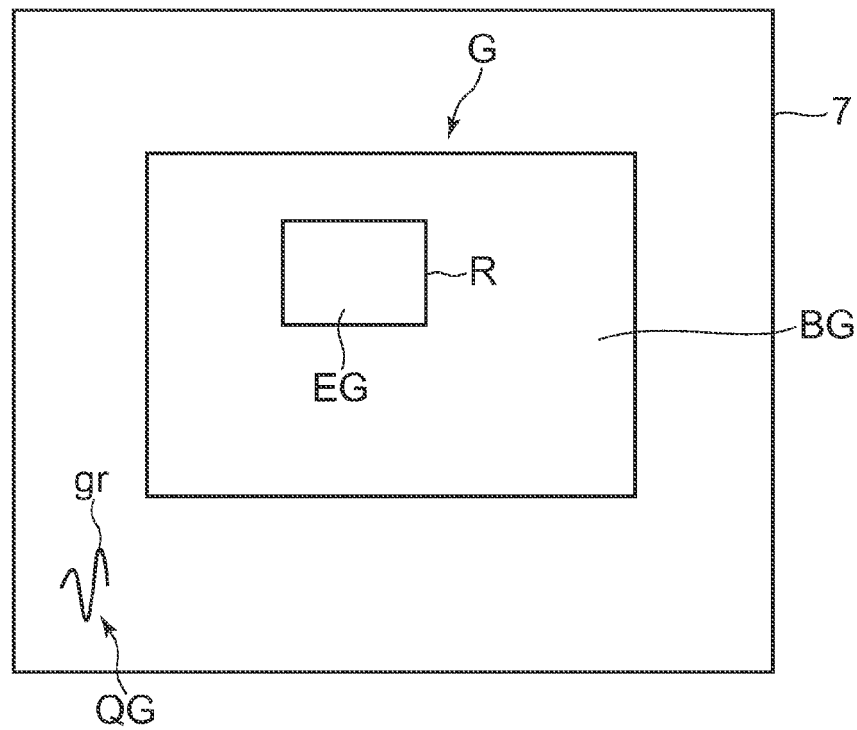
FIG. 7 shows one example of a display of the display unit and is a diagram for describing that a quality indication is displayed so as to flow from left to right with the elapse of time.
Figure 8:
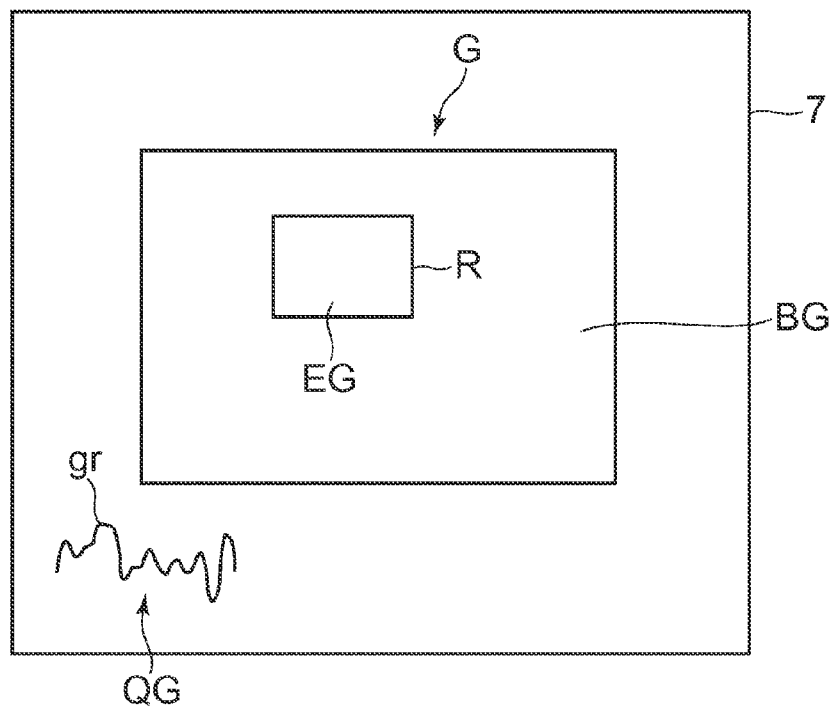
FIG. 8 illustrates one example of a display of the display unit and is a diagram for describing that a quality indication is displayed so as to flow from left to right with the elapse of time.
Figure 9:
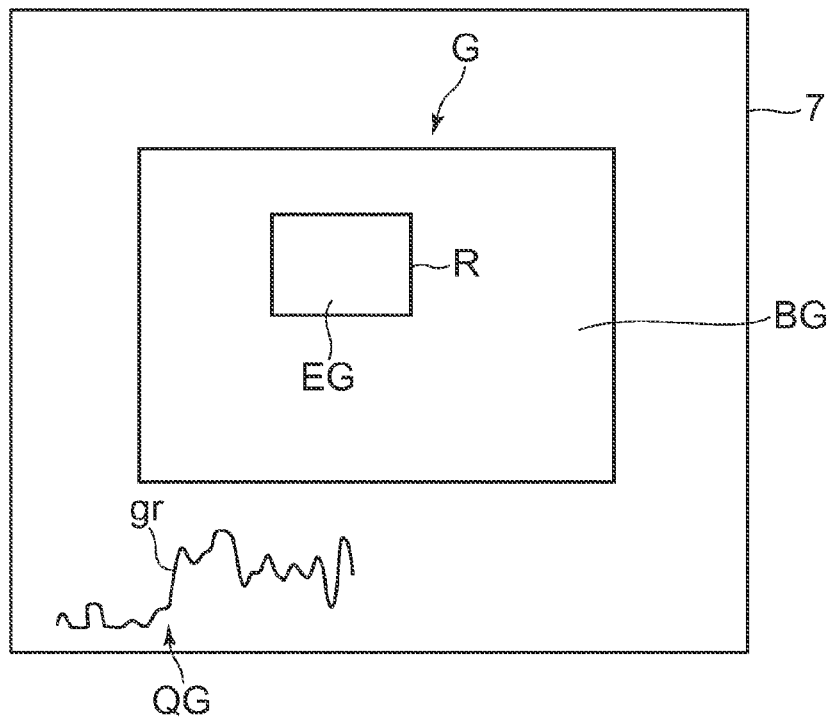
FIG. 9 depicts one example of a display of the display unit and is a diagram for describing that a quality indication is displayed so as to flow left to right with the elapse of time.

The quality indication QG will be explained in further detail. When the ultrasonic image G is represented in a moving picture, the quality indication generator 10 plots, every frame, quality values Qn at an ultrasonic image G being displayed at present to thereby produce the graph gr. Thus, at the display unit 7, the graph gr is displayed so as to flow from left to right with the elapse of time as shown in FIGS. 7, 8 and 9.

Figure 10:
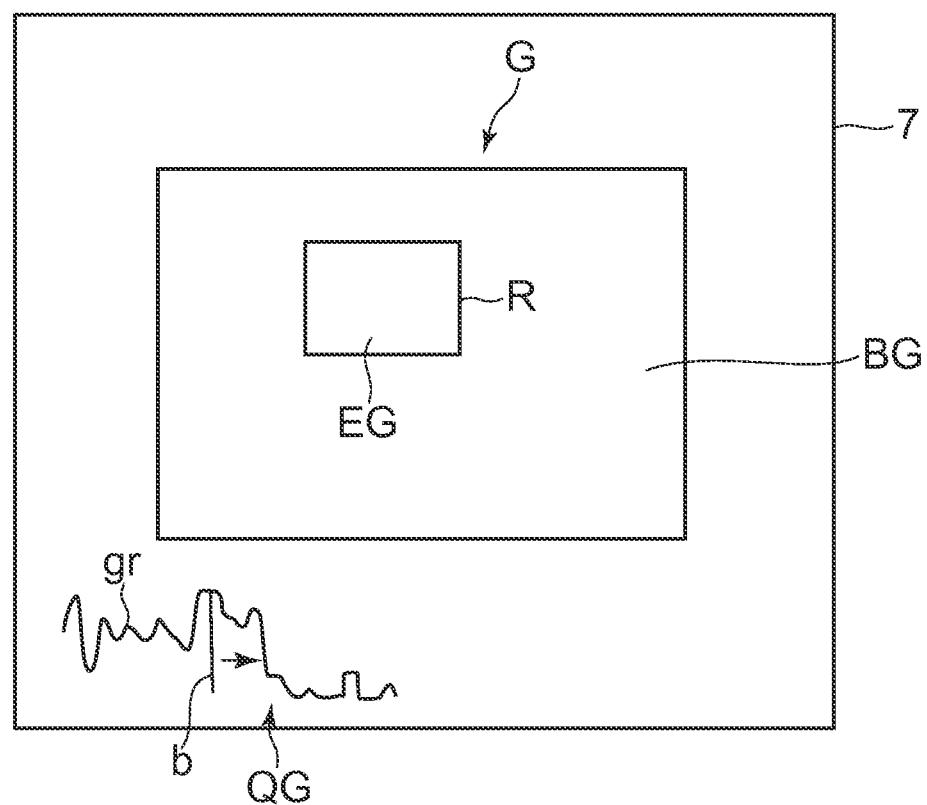
FIG. 10 shows one example of a display of the display unit and is a diagram illustrating another example of a quality indication.

When, however, the ultrasonic image G is of a moving picture formed based on the echo signals stored as the raw data in the storage unit (not shown), the quality indication generator 10 forms a graph gr from the beginning of its reproduction to its end and may allow the display unit 7 to display it. In this case, as shown in FIG. 10, the quality indication QG may include, in addition to the graph gr, a vertical line segment b indicative of whether the present-displayed ultrasonic image G corresponds to one corresponding to a frame of any time. This line segment b moves from left to right during the reproduction of the ultrasonic image G (in the direction indicated by arrow in the figure).

Incidentally, the length of the line segment b becomes a length between the minimum and maximum values of the quality value Qn calculated for every frame at the quality indication generator 10.

According to the ultrasonic diagnostic apparatus 1 of the present embodiment, the quality indication QG comprised of the graph gr indicative of changes in the time of the quality values Qn each calculated based on the ratio Ra of the average value $Xr_{AV}$ to the ideal value $Xi_{AV}$ is represented. Therefore, the operator is able to easily determine whether the degrees of the pressure to the biological tissue by the ultrasonic probe 2 and its relaxation are insufficient or excessive. It is thus possible to evaluate from a broader standpoint than conventional one whether the elastic image on which the elasticity of the biological tissue has accurately been reflected is acquired.

The operator may freeze the ultrasonic image G at a location high in the quality value Qn by looking at the graph gr and output the ultrasonic image G by printing or the like. Consequently, an ultrasonic image on which the elasticity of a biological tissue has been reflected more accurately can be outputted by means of printing or the like. Further, when the ultrasonic image G is being displayed in real time, the operator is also able to adjust the degrees the pressure to the biological tissue by the ultrasonic probe 2 and its relaxation by looking at the graph gr.

A modification of the first embodiment will next be explained. In the modification, the physical quantity average unit 8 selects correlation windows wherein a correlation arithmetic operation in which a correlation coefficient C (0≤C≤1) is greater than or equal to a predetermined threshold value $C_{TH}$, has been performed, and calculates the average of their displacements, thereby acquiring an average value $Xr_{AV'}$. Then, the ratio calculator 9 calculates the ratio Ra using the average value $Xr_{AV'}$ and calculates Y using the equation (1). Further, the quality indication generator 10 forms the quality indication QG using the calculated value Y.

The average value $Xr_{AV'}$ is of an average value obtained by eliminating portions low in correlation coefficient, such as a portion insufficient in the intensity of each echo signal, a portion having produced a lateral shift of a biological tissue, etc. Accordingly, the quality value Qn obtained from such an average value $Xr_{AV'}$ is indicative of whether the pressure by the ultrasonic probe 2 and its relaxation are being carried out with suitable intensity. Thus, the operator is able to more accurately grasp from the quality indication QG whether the pressure by the ultrasonic probe 2 and its relaxation are being performed with suitable intensity. For example, when the quality value Qn is away from 1, the operator is capable of grasping that the pressure by the ultrasonic probe 2 and its relaxation are not being performed with suitable intensity. On the other hand, if the quality value Qn is 1 or a value close to 1, then the operator is able to grasp that the pressure by the ultrasonic probe 2 is being performed with suitable intensity.

If the calculation of the average value $Xr_{AV}$ is done inclusive of the displacements obtained by the correlation arithmetic operation low in the correlation coefficient, then the average value $Xr_{AV}$ becomes small and the quality value Qn is away from 1 where, for example, the intensity of each echo signal is weak, even though the degrees of the pressure to the biological tissue by the ultrasonic probe 2 and its relaxation are suitable. Thus, if the degrees of the pressure to the biological tissue by the ultrasonic probe 2 and its relaxation are suitable by calculating the average value $Xr_{AV}$ except for the displacement of each portion low in correlation coefficient, as in the case of this modification, the quality value Qn always becomes near 1. It is thus possible to display the quality indication QG on which whether the degrees of the pressure to the biological tissue and its relaxation are suitable has been reflected more accurately.

Second Embodiment

Figure 11:
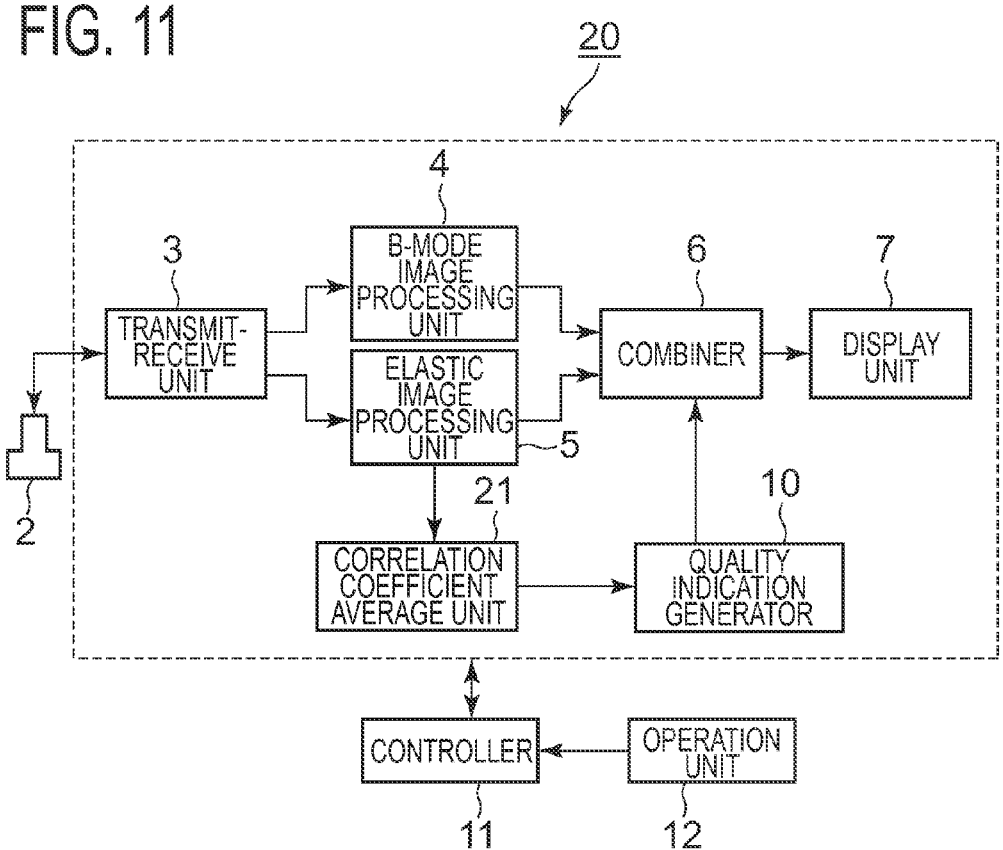
FIG. 11 is a block diagram showing a schematic configuration of a second embodiment of an ultrasonic diagnostic apparatus according to the invention.
Figure 12:
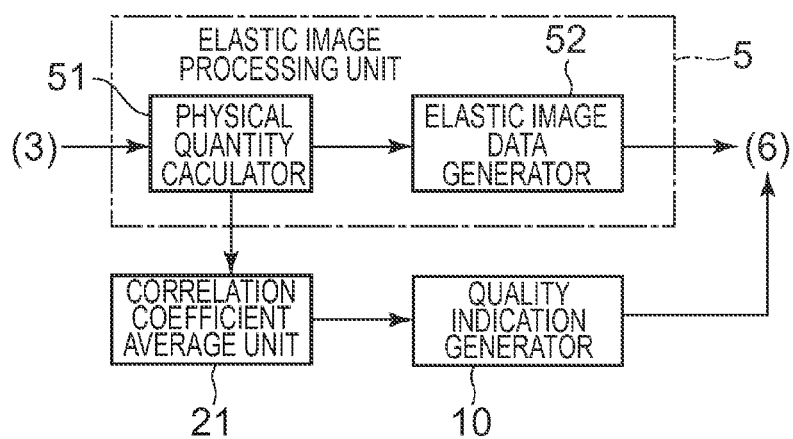
FIG. 12 is a block diagram illustrating a fragmentary configuration of the ultrasonic diagnostic apparatus shown in FIG. 11.

A second embodiment will next be explained based on FIGS. 11 and 12. Incidentally, the same reference numerals are respectively attached to the same components as those in the first embodiment, and their explanations will therefore be omitted.

An ultrasonic diagnostic apparatus 20 according to the present embodiment is not equipped with the physical quantity average unit 8 and the ratio calculator 9, but equipped with a correlation coefficient average unit 21 instead of them. The correlation coefficient average unit 21 is one example illustrative of an embodiment of the correlation average unit 21 in the invention.

The operation of the ultrasonic diagnostic apparatus 20 according to the present embodiment will be explained. The present embodiment is different from the first embodiment in the method for generating the quality indication QG. Described concretely, the correlation coefficient average unit 21 calculates, for every frame, average values $C_{AV}$ in regions of interest R (regions R(i) and R(ii)), of correlation coefficients C at respective correlation arithmetic operations performed by the physical quantity calculator 51 upon formation of the quality indication QG. In the present embodiment, each average value $C_{AV}$ of the correlation coefficients C is assumed to be a quality value Qn. Since 0≤C≤1 herein, 0≤Qn≤1 is established even in the present embodiment. At the correlation coefficient at each correlation arithmetic operation, a displacement on which the elasticity of a biological tissue has been reflected accurately, can be obtained as it approaches 1. On the other hand, a displacement on which the elasticity of the biological tissue has been reflected accurately cannot be obtained as it approaches zero. Thus, even in the present embodiment, the quality of an elastic image EG becomes satisfactory as Qn approaches 1, whereas as Qn approaches zero, the quality of the elastic image EG becomes worse.

Then, the quality indication generator 10 plots the average values $C_{AV}$ as the quality values Qn and forms a quality indication QG comprised of the graph gr. At this time, the quality indication generator 10 may calculate the averages corresponding to plural frames, of the quality values Qn in a manner similar to the first embodiment and plot their average values.

Even in the present embodiment, the graph gr that configures the quality indication QG may be displayed so as to flow from left to right with the elapse of time in a manner similar to the first embodiment. The quality indication QG may include a vertical line segment b in addition to the graph gr.

According to the ultrasonic diagnostic apparatus 20 of the present embodiment, a quality indication QG comprised of a graph gr indicative of changes in the time of quality values Qn each corresponding to an average value $C_{AV}$ of correlation coefficients C is displayed. Therefore, an operator can grasp whether a displayed elastic image is of an image of elastic image data generated based on displacements each obtained by a correlation arithmetic operation low in correlation coefficient due to the fact that, for example, the pressure to a biological tissue and its relaxation are excessive and the intensity of each echo signal is insufficient. It is thus possible to evaluate from a standpoint different from conventional one whether the displayed image is of an image on which an elastic image of a biological tissue has been reflected accurately.

Third Embodiment

Figure 13:
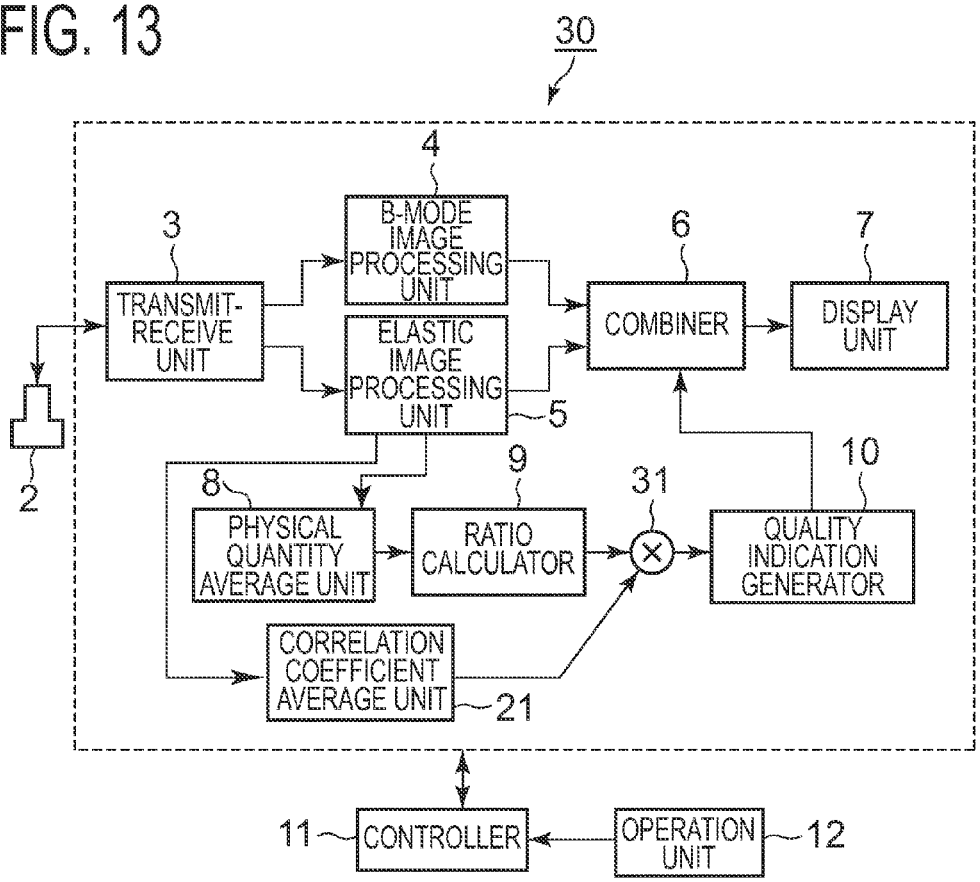
FIG. 13 is a block diagram depicting a schematic configuration of a third embodiment of an ultrasonic diagnostic apparatus according to the invention.
Figure 14:
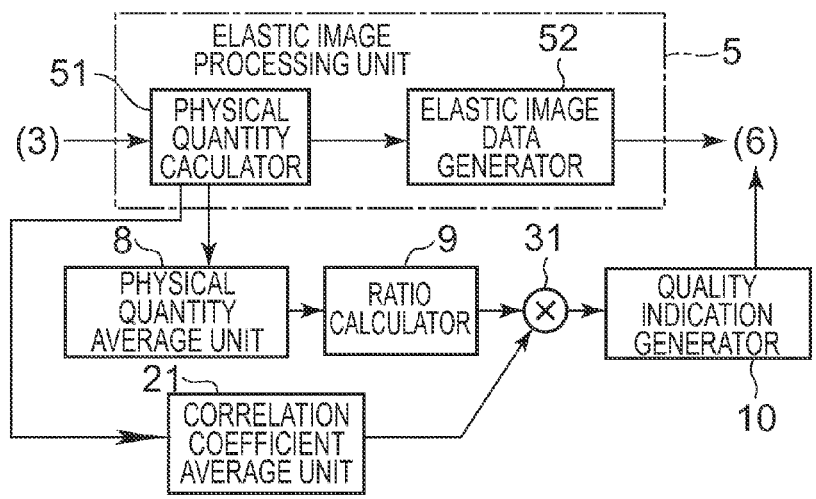
FIG. 14 is a block diagram showing a fragmentary configuration of the ultrasonic diagnostic apparatus shown in FIG. 13.

A third embodiment will next be explained based on FIGS. 13 and 14. Incidentally, the same reference numerals are respectively attached to the same components as those in the first and second embodiment, and their explanations will therefore be omitted.

An ultrasonic diagnostic apparatus 30 of the present embodiment is equipped with the physical quantity average unit 8, ratio calculator 9, quality indication generator 10, correlation coefficient average unit 21 and the like. Further, the ultrasonic diagnostic apparatus 30 further includes a multiplier 31. The multiplier 31 is one example illustrative of an embodiment of a multiplier in the invention.

The generation of the quality indication QG at the ultrasonic diagnostic apparatus 30 of the present embodiment will be explained. The physical quantity average unit 8 selects correlation windows wherein a correlation arithmetic operation in which a correlation coefficient C is greater than or equal to a predetermined threshold value $C_{TH}$, has been performed, and calculates an average value $Xr_{AV'}$ of their displacements in manner similar to the modification of the first embodiment. The ratio calculator 9 calculates the ratio Ra using the average value $Xr_{AV'}$ and calculates Y from the equation (1). In a manner similar to the second embodiment, the correlation coefficient average unit 21 calculates an average value $C_{AV}$ of correlation coefficients.

The multiplier 31 multiplies the calculated value Y obtained at the ratio calculator 9 and the average value $C_{AV}$ of the correlation coefficients obtained at the correlation coefficient average unit 21 by each other to calculate a multiplied value M. The multiplied value M is calculated for every frame.

Here, when the calculated value Y and the average value $C_{AV}$ of the correlation coefficients are multiplied by each other, the multiplier 31 may assign weights thereto to thereby multiply them by each other.

The quality indication generator 10 plots the multiplied values M calculated every frame as the quality values Qn to thereby form the quality indication QG. At this time, the quality indication generator 10 may calculate the averages corresponding to plural frames, of the quality values Qn and plot their average values in a manner similar to the first and second embodiments.

Even in the present embodiment, a graph gr that configures the quality indication QG may be displayed so as to flow from left to right with the elapse of time in a manner similar to the first and second embodiments. The quality indication QG may include a vertical line segment b in addition to the graph gr.

Since $0 \le Y \le 1$ and $0 \le C_{AV} \le 1$, M assumes $0 \le M \le 1$. Thus, even in the present embodiment, Qn assumes $0 \le Qn \le 1$. Since the multiplied value M is of the value obtained by multiplying the calculated value Y and the average value $C_{AV}$ of the correlation coefficients by each other, the quality of an elastic image EG becomes satisfactory as the multiplied value M, i.e., Qn approaches 1, whereas the quality of the elastic image EG becomes worse as Qn approaches zero.

Now, when the quality values Qn each calculated from the average value $Xr_{AV'}$ of the displacements obtained by the correlation arithmetic operation on the correlation coefficients each greater than or equal to the predetermined threshold value $C_{TH}$ are displayed as the quality indication QG as in the modification of the first embodiment, the correlation coefficients are not completely reflected as elements for evaluation of the quality of the elastic image. On the other hand, when the average value $C_{AV}$ of the correlation coefficients C is displayed as the quality indication QG as in the second embodiment, each correlation coefficient C becomes high even if the degrees of the pressure to the biological tissue by the ultrasonic probe 2 and its relaxation are insufficient. Therefore, the satisfactory value may be represented as the quality value Qn. Thus, in the present embodiment, the calculated value Y obtained using the ratio Ra calculated using the average value $Xr_{AV'}$, and the average value $C_{AV}$ of the correlation coefficients C are multiplied by each other, thereby making it possible to display a quality indication QG to which elements for the degrees of pressure to a biological tissue and its relaxation and elements for correlation coefficients are added. It is thus possible to evaluate from a broader standpoint than conventional one whether an elastic image on which the elasticity of a biological tissue has been reflected accurately is reached.

Fourth Embodiment

Figure 15:
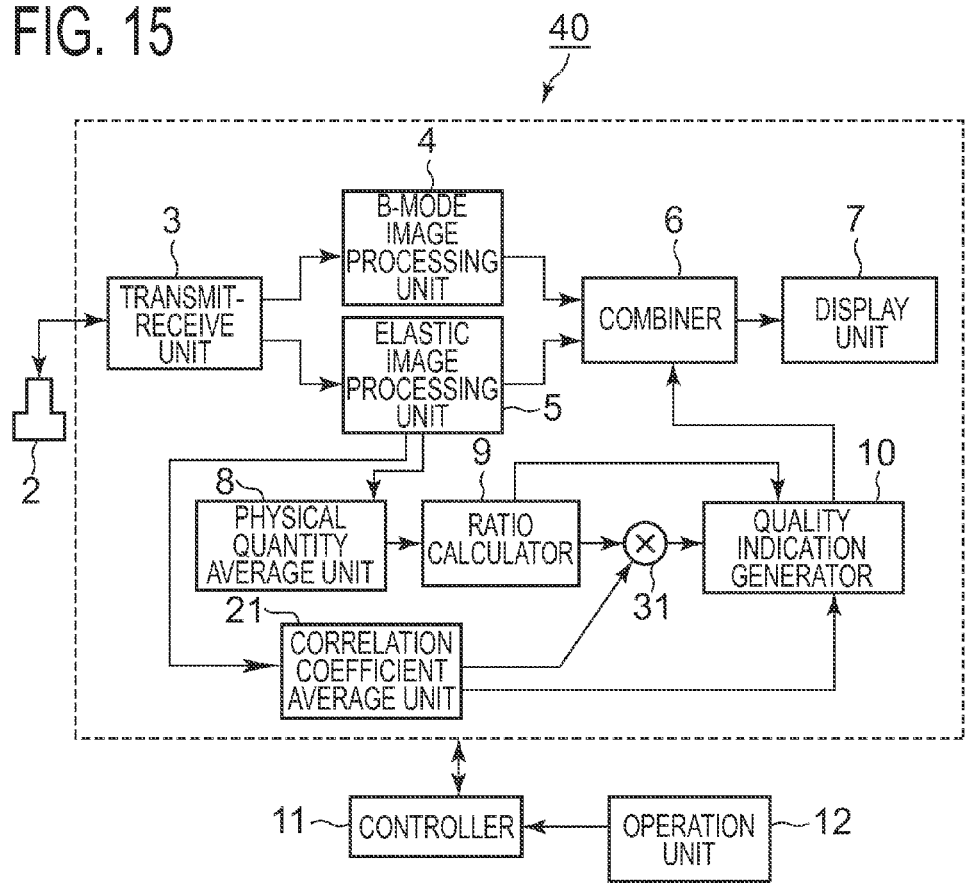
FIG. 15 is a block diagram depicting a schematic configuration of a fourth embodiment of an ultrasonic diagnostic apparatus according to the invention.
Figure 16:
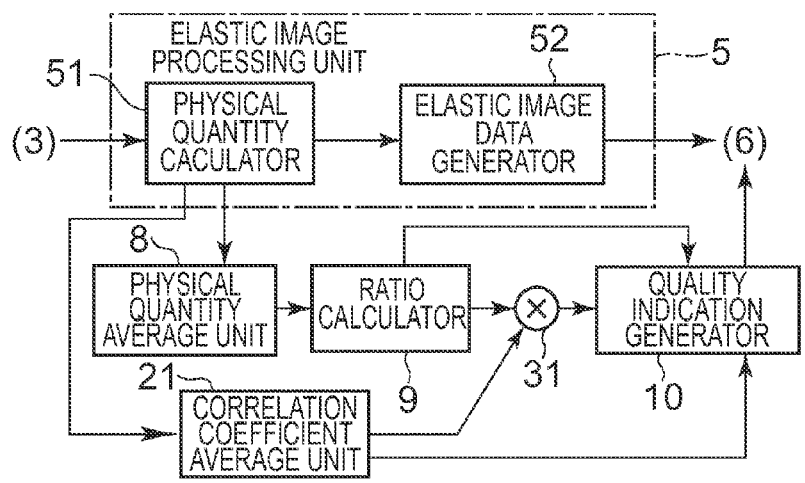
FIG. 16 is a block diagram showing a fragmentary configuration of the ultrasonic diagnostic apparatus shown in FIG. 15.

A fourth embodiment will next be explained based on FIGS. 15 and 16. Incidentally, the same reference numerals are respectively attached to the same components as those in the first through third embodiments, and the description thereof will therefore be omitted.

An ultrasonic diagnostic apparatus 40 of the present embodiment is identical in basic configuration to the ultrasonic diagnostic apparatus 30 of the third embodiment. In the present embodiment, however, any of the calculated value Y obtained at the ratio calculator 9, the average value $C_{AV}$ of the correlation coefficients obtained at the correlation coefficient average unit 21 and the multiplied value M obtained at the multiplier 31 is selected as a quality value Qn. The quality indication generator 10 displays a quality indication QG.

Described concretely, whether the display of the quality indication QG should be performed using any of the calculated value Y, the average value $C_{AV}$ of the correlation coefficients and the multiplied value M is inputted by an operator at the operation unit 12. Then, the controller 11 performs control, based on the instructed input from the operation unit 12 to perform any of the calculation of the calculated value Y by the ratio calculator 9, the calculation of the average value $C_{AV}$ of the correlation coefficients by the correlation coefficient average unit 21 and the calculation of the value M multiplied by the multiplier 31, thereby executing the generation of a quality indication QG by the quality indication generator 10 based on the calculated values obtained. Consequently, the quality indication QG generated using the values that belong to the type selected by the operator is displayed on the display unit 7.

The operator may perform the input of instructions through the operation unit 12 to thereby change the type of value temporarily selected out of the calculated value Y, the average value $C_{AV}$ of the correlation coefficients and the multiplied value M. By performing the changeover instruction input through the operation unit 12, a quality indication QG generated using values that belong to the newly-selected type is displayed on the display unit 7.

According to the ultrasonic diagnostic apparatus 40 of the present embodiment, the quality indication QG generated using the calculated Y obtained at the ratio calculator 9, the quality indication QG generated using the average value $C_{AV}$ of the correlation coefficients obtained at the correlation coefficient average unit 21 and the quality indication QG generated using the multiplied value M obtained at the multiplier 31 can be displayed by switching. It is therefore possible to evaluate from a broader standpoint than conventional one whether an elastic image on which the elasticity of a biological tissue has been reflected accurately, is brought about.

Although the invention has been explained by the respective embodiments as above, the invention can of course be changed in various ways within the scope not departing from the gist thereof. For example, the physical quantity calculator 51 may calculate distortion of a biological tissue or its elastic modulus as a physical quantity related to the elasticity of the biological tissue instead of the displacement due to the deformation of the biological tissue.

The ratio calculator 9 calculates only the ratio Ra and may not perform the arithmetic operation of (equation (1)). In this case, the quality indication generator 10 may generate a graph gr formed by plotting the ratio |Ra| as each quality value Qn, as the quality indication QG.

Figure 17:
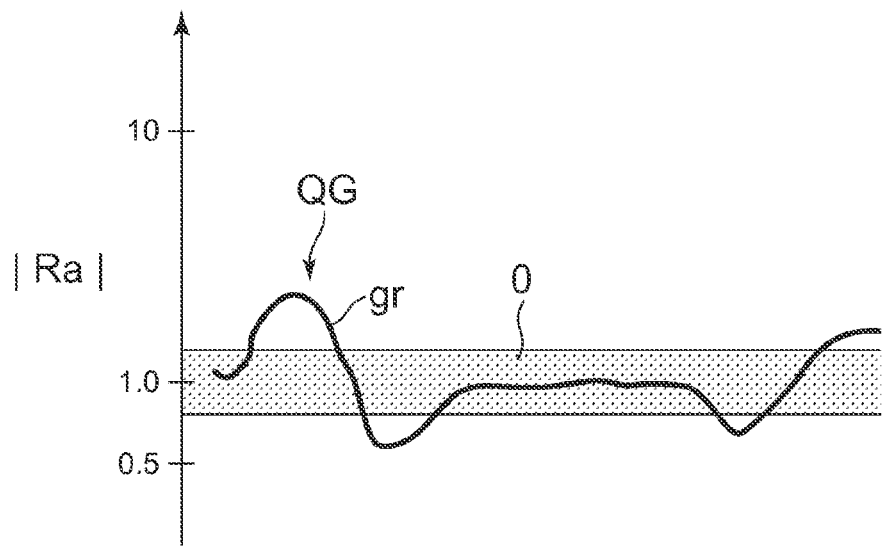
FIG. 17 is a diagram illustrating another example of a quality indication.

One example of a quality indication QG formed by plotting the ratio |Ra| as the quality value Qn and displayed on the display unit 7 is shown in FIG. 17. In FIG. 17, the horizontal axis indicates time, and the vertical axis indicates a ratio |Ra|. As shown in FIG. 17, a band-like portion O may be disposed in a predetermined range in which the ratio |Ra| is near 1. The band-like portion O is set to within a range of a ratio |Ra| at which an elastic image EG on which the elasticity of a biological tissue has been reflected accurately is obtained. If the operator performs pressure to the biological tissue by the ultrasonic probe 2 and its relaxation in such a manner that the quality indication QG falls within the band-like portion O by displaying such a band-like portion O, it is then possible to obtain an elastic image on which the elasticity of the biological tissue has been reflected accurately.

Figure 18:
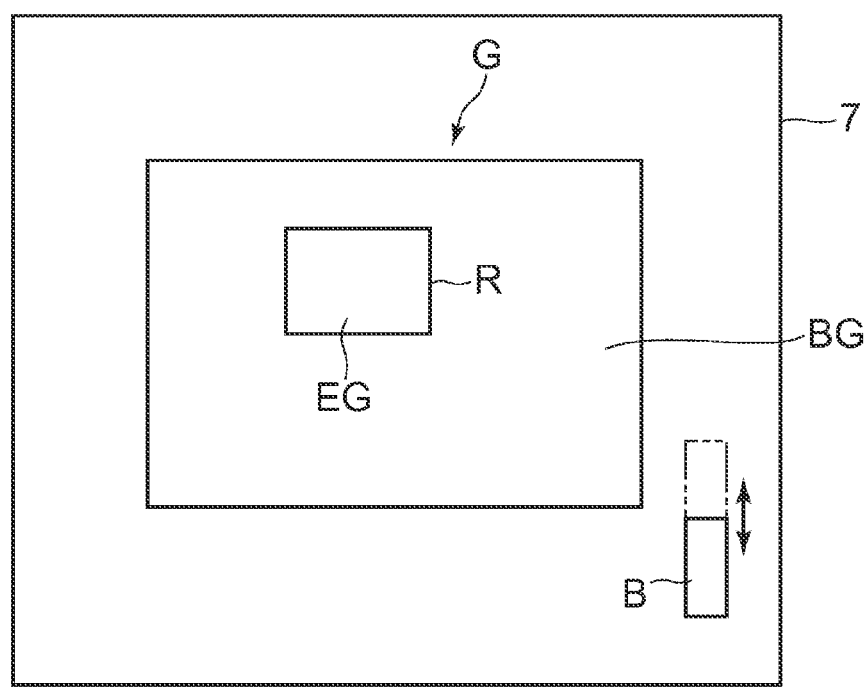
FIG. 18 is a diagram showing a display unit that has displayed a further example of a quality indication.

The quality indication QG is not limited to one comprised of the graph gr, but may be one comprised of a bar B as shown in FIG. 18, for example. The bar B is equivalent to a value (0≤Qn≤1) of the quality value Qn in vertical length and expands and contracts in the vertical direction with a change in the quality value Qn.

The bar B may be one that changes in color according to the quality value Qn, which is other than one that expands and contracts in the vertical direction according to the quality value Qn.

In addition, the quality indication QG may be displayed on the display unit 7 in numeric values. Further, the quality value Qn is not limited to one represented as the quality indication QG. For example, there may be provided a speaker (not shown) for producing the quality value Qn as a sound. The speaker is one example illustrative of an embodiment of a notification unit in the invention. In this case, the high and low levels of the quality value Qn are expressed in the pitch of a sound.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic diagnostic apparatus comprising:
at least one hardware processor configured to:
set correlation windows to two echo signals obtained by transmission and reception of ultrasound to and from a biological tissue and different in time on the same sound rays;
perform a correlation arithmetic operation between the correlation windows to calculate physical quantities related to elasticity of respective regions in the biological tissue;
generate elastic image data of the biological tissue with respect to an elastic image forming region of a transmission/reception surface of the ultrasound based on the physical quantities;
calculate an average value ($Xr_{AV}$) of the physical quantities in the elastic image forming region for every frame;
calculate a ratio (Ra) of the average value ($Xr_{AV}$) to a preset average value ($Xi_{AV}$) of the physical quantities, wherein the preset average value ($Xi_{AV}$) of the physical quantities corresponds to an ideal value when at least one of a pressure and a relaxation of the biological tissue is performed by an ultrasonic probe of the ultrasonic diagnostic apparatus, and wherein the calculated ratio (Ra) is indicative of whether the pressure and the relaxation are being performed with suitable intensity; and
indicate the calculated ratio.

2. The ultrasonic diagnostic apparatus according to claim 1, wherein the at least one hardware processor is configured to calculate the average value ($Xr_{AV}$) of physical quantities obtained with respect to the correlation windows in which the correlation arithmetic operation is performed using correlation coefficients each greater than or equal to a predetermined threshold value.

3. The ultrasonic diagnostic apparatus according to claim 1, wherein the calculated ratios (Ra) obtained for every frame, by the at least one hardware processor, are averaged over a plurality of frames and transmitted to a notification unit.

4. The ultrasonic diagnostic apparatus according to claim 1, further comprising a notification unit configured to indicate the calculated ratio (Ra) by at least any one of a graph, a bar, color, a numeric value, and a pitch of a sound.

5. An ultrasonic diagnostic apparatus comprising:
at least one hardware processor configured to:
set correlation windows to two echo signals obtained by transmission and reception of ultrasound to and from a biological tissue and different in time on the same sound rays;
perform a correlation arithmetic operation between the correlation windows to calculate physical quantities related to elasticity of respective regions in the biological tissue;
generate elastic image data of the biological tissue with respect to an elastic image forming region of a transmission/reception surface of the ultrasound based on the physical quantities;
calculate, for every frame in the elastic image forming region, an average value ($C_{AV}$) of correlation coefficients at the correlation arithmetic operation between the correlation windows;
calculate a ratio (Ra) of the average value ($C_{AV}$) to a preset average value ($Xi_{AV}$) of the physical quantities, wherein the preset average value ($Xi_{AV}$) of the physical quantities corresponds to an ideal value when at least one of a pressure and a relaxation of the biological tissue is performed by an ultrasonic probe of the ultrasonic diagnostic apparatus, and wherein the calculated ratio (Ra) is indicative of whether the pressure and the relaxation are being performed with suitable intensity; and indicate the calculated ratio (Ra).

6. The ultrasonic diagnostic apparatus according to claim 5, wherein the average values ($C_{AV}$) of correlation coefficients obtained for every frame are averaged over a plurality of frames and transmitted to a notification unit.

7. The ultrasonic diagnostic apparatus according to claim 5, further comprising a notification unit configured to indicate the calculated ratio (Ra) by at least any one of a graph, a bar, color, a numeric value, and a pitch of a sound.

8. An ultrasonic diagnostic apparatus comprising:
at least one hardware processor configured to:
calculate physical quantities related to elasticity of respective regions in a biological tissue based on two echo signals obtained by transmission and reception of ultrasound to and from the biological tissue and different in time on the same sound rays;
generate elastic image data of the biological tissue with respect to an elastic image forming region of a transmission/reception surface of the ultrasound based on the physical quantities;
calculate, for every frame in the elastic image forming region, an average value ($Xr_{AV}$) of the physical quantities obtained with respect to correlation windows in which a correlation arithmetic operation is performed using correlation coefficients greater than or equal to a predetermined threshold value;
calculate a ratio (Ra) of the average ($Xr_{AV}$) to a preset average value ($Xi_{AV}$) of the physical quantities, wherein the preset average value ($Xi_{AV}$) of the physical quantities corresponds to an ideal value when at least one of a pressure and a relaxation of the biological tissue is performed by an ultrasonic probe of the ultrasonic diagnostic apparatus, and wherein the calculated ratio (Ra) is indicative of whether the pressure and the relaxation are being performed with suitable intensity;
calculate, for every frame in the elastic image forming region, an average value ($C_{AV}$) of the correlation coefficients at the correlation arithmetic operation between the correlation windows;
multiply the calculated ratio (Ra) and the calculated average value ($C_{AV}$) by each other; and
indicate the multiplication.

9. The ultrasonic diagnostic apparatus according to claim 8, wherein the at least one hardware processor is configured to perform a weighted arithmetic operation on the calculated ratio (Ra) and the calculated average value ($C_{AV}$).

10. The ultrasonic diagnostic apparatus according to claim 8, wherein the multiplications obtained for every frame are averaged over a plurality of frames and transmitted to a notification unit.

11. The ultrasonic diagnostic apparatus according to claim 10, wherein the at least one hardware processor is configured to perform a weighted arithmetic operation on the calculated ratio (Ra) and the calculated average value ($C_{AV}$).

12. The ultrasonic diagnostic apparatus according to claim 8, further comprising a notification unit configured to indicate the multiplication by at least any one of a graph, a bar, color, a numeric value, and a pitch of a sound.

13. An ultrasonic diagnostic apparatus comprising:
at least one hardware processor configured to:
calculate physical quantities related to elasticity of respective regions in a biological tissue based on two echo signals obtained by transmission and reception of ultrasound to and from the biological tissue and different in time on the same sound rays;
generate elastic image data of the biological tissue in an elastic image forming region of a transmission/reception surface of the ultrasound based on the physical quantities;
calculate, for every frame in the elastic image forming region, an average value ($Xr_{AV}$) of the physical quantities obtained with respect to correlation windows in which a correlation arithmetic operation is performed using correlation coefficients greater than or equal to a predetermined threshold value;
calculate a ratio (Ra) of the average value($Xr_{AV}$) to a preset average value ($Xi_{AV}$) of the physical quantities, wherein the preset average value ($Xi_{AV}$) of the physical quantities corresponds to an ideal value when at least one of a pressure and a relaxation of the biological tissue is performed by an ultrasonic probe of the ultrasonic diagnostic apparatus, and wherein the calculated ratio (Ra) is indicative of whether the pressure and the relaxation are being performed with suitable intensity;
calculate, for every frame in the elastic image forming region, an average value ($C_{AV}$) of the correlation coefficients at the correlation arithmetic operation between the correlation windows;
multiply the calculated ratio (Ra) and the calculated average value ($C_{AV}$) by each other;
indicate at least one of the calculated ratio (Ra), the calculated average value ($C_{AV}$), and the multiplication; and
input instructions for switching to a notification unit.

14. The ultrasonic diagnostic apparatus according to claim 13, further comprising a notification unit configured to indicate at least one of the the calculated ratio (Ra), the calculated average value ($C_{AV}$), and the multiplication by at least any one of a graph, a bar, color, a numeric value, and a pitch of a sound.

15. A method of generating an elastic image comprising the steps of:
setting, by at least one hardware processor, correlation windows to two echo signals obtained by transmission/reception of ultrasound to and from a biological tissue and different in time on the same sound rays;
performing, by the at least one hardware processor, a correlation arithmetic operation between the correlation windows to thereby calculate physical quantities related to elasticity of respective regions in the biological tissue;
generating, by the at least one hardware processor, elastic image data of the biological tissue with respect to an elastic image forming region of a transmission/reception surface of the ultrasound based on the physical quantities;
calculating, by the at least one hardware processor, an average value ($Xr_{AV}$) of the physical quantities in the elastic image forming region for every frame;
calculating, by the at least one hardware processor, a ratio (Ra) of the average value ($Xr_{AV}$) and a preset average value ($Xi_{AV}$) of the physical quantities, wherein the preset average value ($Xi_{AV}$) of the physical quantities corresponds to an ideal value when at least one of a pressure and a relaxation of the biological tissue is performed by an ultrasonic probe, and wherein the calculated ratio (Ra) is indicative of whether the pressure and the relaxation are being performed with suitable intensity; and
indicating the calculated ratio (Ra).

16. A method of generating an elastic image comprising the steps of:
setting, by at least one hardware processor, correlation windows to two echo signals obtained by transmission and reception of ultrasound to and from a biological tissue and different in time on the same sound rays and performing a correlation arithmetic operation between the correlation windows to thereby calculate physical quantities related to elasticity of respective regions in the biological tissue;

generating bye at least one hardware processor, elastic image data of the biological tissue with respect to an elastic image forming region of a transmission/reception surface of the ultrasound based on the physical quantities;

calculating, by the at least one hardware processor, for every frame in the elastic image forming region an average value ($C_{AV}$) of correlation coefficients at the correlation arithmetic operation between the correlation windows;

calculating, by the at least one hardware processor, a ratio (Ra) of the average value ($C_{AV}$) and a preset average value ($Xi_{AV}$) of the physical quantities, wherein the preset average value) ($Xi_{AV}$) of the physical quantities corresponds to an ideal value when at least one of a pressure and a relaxation of the biological tissue is performed by an ultrasonic probe, and wherein the calculated ratio (Ra) is indicative of whether the pressure and the relaxation are being performed with suitable intensity; and indicating the calculated ratio (Ra).

* * * * *